United States Patent
White et al.

(10) Patent No.: US 8,465,490 B1
(45) Date of Patent: Jun. 18, 2013

(54) DISPOSABLE NEUCLEOTOMY SHAVER

(75) Inventors: Patrick M. White, West Chester, PA (US); Robert Siegler, Williamsville, NY (US); James Hetherwick, Lambertville, MI (US)

(73) Assignee: Greatbatch Ltd., Clarence, NY (US)

( * ) Notice: Subject to any disclaimer, the term of this patent is extended or adjusted under 35 U.S.C. 154(b) by 196 days.

(21) Appl. No.: 13/015,714

(22) Filed: Jan. 28, 2011

Related U.S. Application Data

(60) Provisional application No. 61/299,703, filed on Jan. 29, 2010.

(51) Int. Cl.
*A61B 17/00* (2006.01)

(52) U.S. Cl.
USPC .............................................. 606/79; 30/206

(58) Field of Classification Search
USPC ................. 606/79–81, 83–85, 167, 170, 174, 606/180, 131–133; 30/43.4–43.6, 279.9
See application file for complete search history.

(56) References Cited

U.S. PATENT DOCUMENTS

| | | | | |
|---|---|---|---|---|
| 2,073,137 A * | 3/1937 | Bimrose | | 433/116 |
| 4,603,694 A * | 8/1986 | Wheeler | | 606/171 |
| 5,810,809 A * | 9/1998 | Rydell | | 606/49 |
| 5,913,867 A * | 6/1999 | Dion | | 606/180 |
| 5,944,691 A * | 8/1999 | Querns et al. | | 604/104 |
| 6,053,928 A * | 4/2000 | Van Wyk et al. | | 606/167 |
| 6,511,483 B1 * | 1/2003 | Gwyther | | 606/79 |
| 6,692,501 B2 | 2/2004 | Michelson | | |
| 7,160,304 B2 | 1/2007 | Michelson | | |
| 7,331,963 B2 * | 2/2008 | Bryan et al. | | 606/80 |
| 7,611,514 B2 | 11/2009 | Michelson | | |
| 7,927,361 B2 * | 4/2011 | Oliver et al. | | 606/279 |
| 7,993,360 B2 * | 8/2011 | Hacker et al. | | 606/180 |
| 8,002,776 B2 * | 8/2011 | Liu et al. | | 606/85 |
| 2005/0015091 A1 * | 1/2005 | Bryan et al. | | 606/80 |
| 2006/0100633 A1 * | 5/2006 | Michelson | | 606/84 |
| 2006/0129160 A1 | 6/2006 | Liu et al. | | |
| 2006/0212060 A1 * | 9/2006 | Hacker et al. | | 606/180 |
| 2008/0200987 A1 * | 8/2008 | Copf, Jr. | | 623/17.16 |
| 2008/0306482 A1 * | 12/2008 | Muller | | 606/79 |
| 2009/0163921 A1 * | 6/2009 | Lechot et al. | | 606/81 |
| 2010/0010525 A1 | 1/2010 | Lockard et al. | | |
| 2010/0234760 A1 * | 9/2010 | Almazan | | 600/566 |
| 2011/0270294 A1 * | 11/2011 | Rubin | | 606/180 |
| 2012/0101513 A1 * | 4/2012 | Shadeck et al. | | 606/170 |

* cited by examiner

*Primary Examiner* — Todd Manahan
*Assistant Examiner* — Eric S Gibson
(74) *Attorney, Agent, or Firm* — Steven W. Winn

(57) ABSTRACT

A spine shaver designed with increased tissue removing efficiency is described. The shaver comprises a cylindrical shaver blade, an elongated body, and a pulley and belt drive mechanism. The shaver blade further comprises a tissue cutting surface that extends along the longitudinal axis of the shaver. The shaver is further designed with the shaver blade positioned perpendicularly to the elongated body. The increased surface area of the shaver blade and perpendicular blade orientation provide an efficient means of removing spinal tissue and debulking the area between two vertebrae.

29 Claims, 9 Drawing Sheets

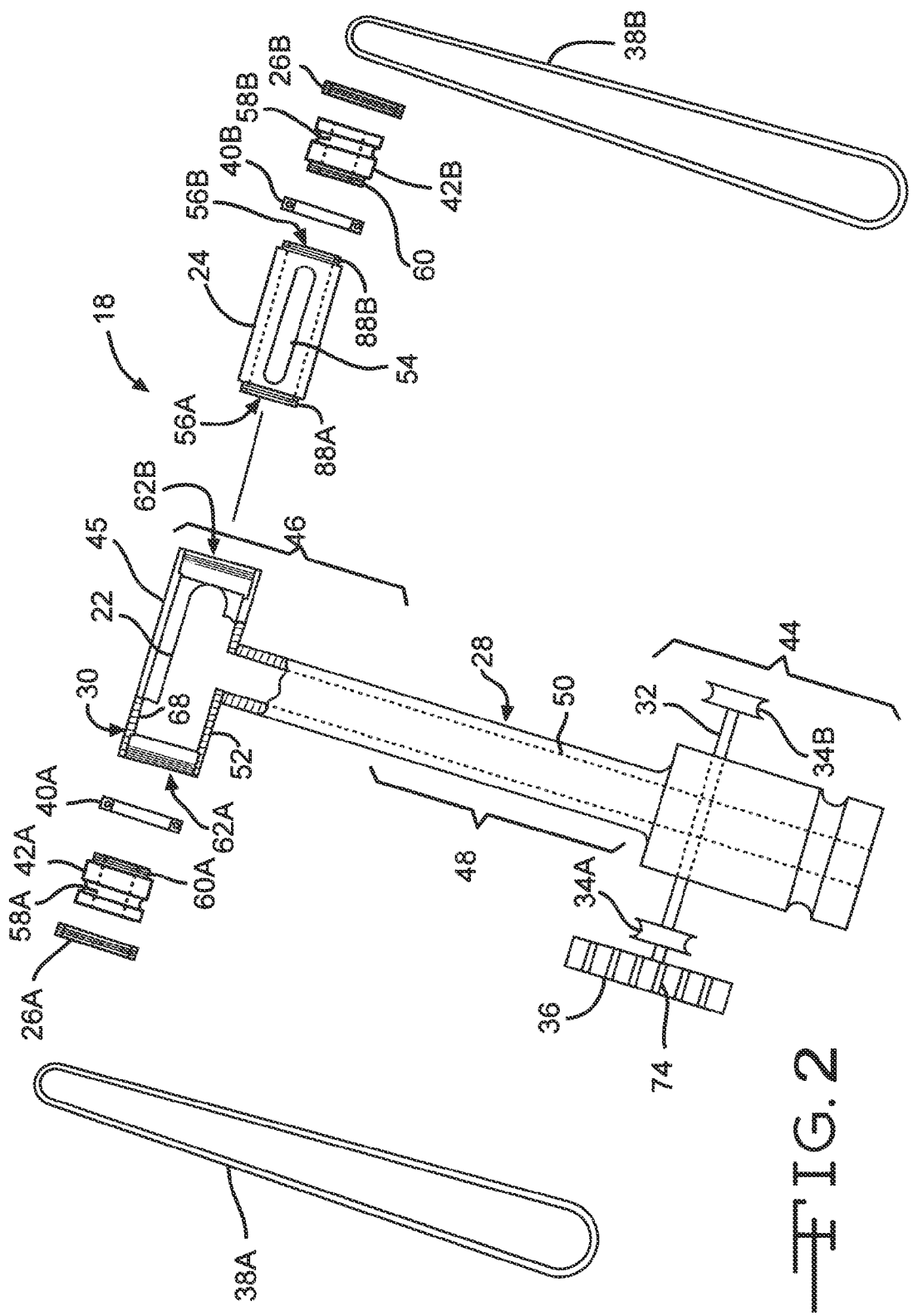

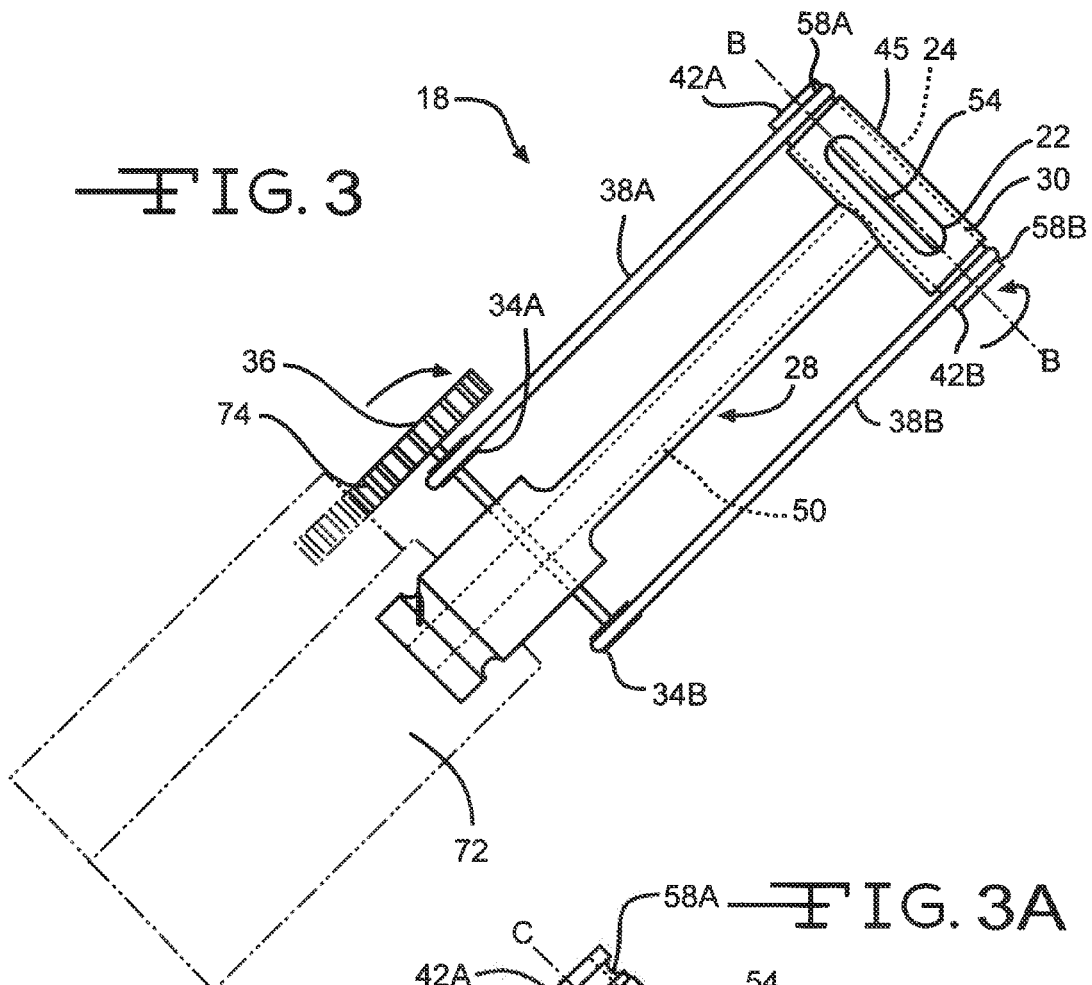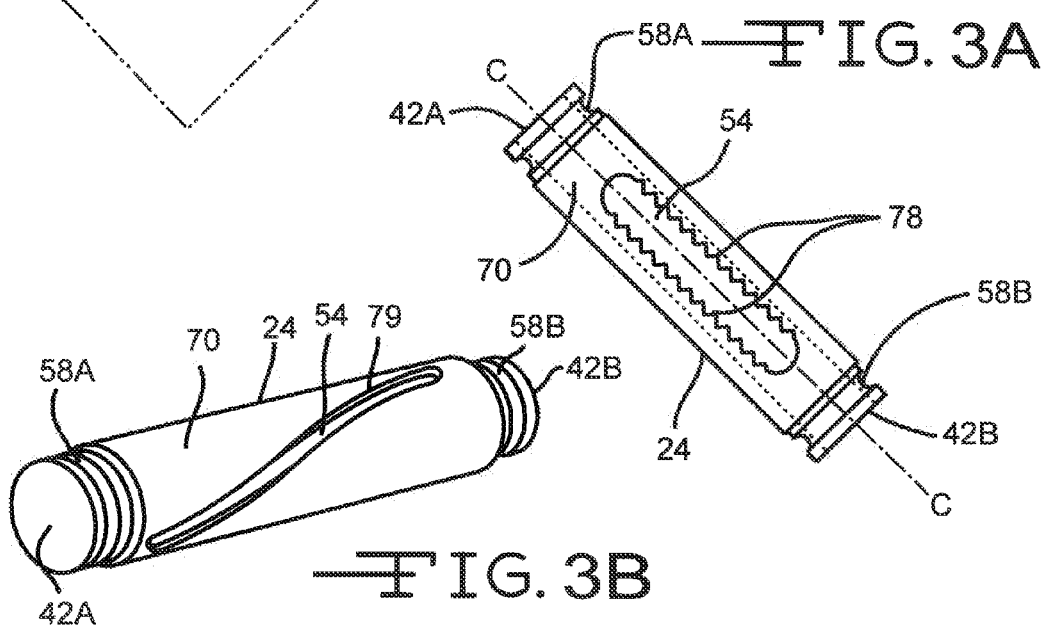

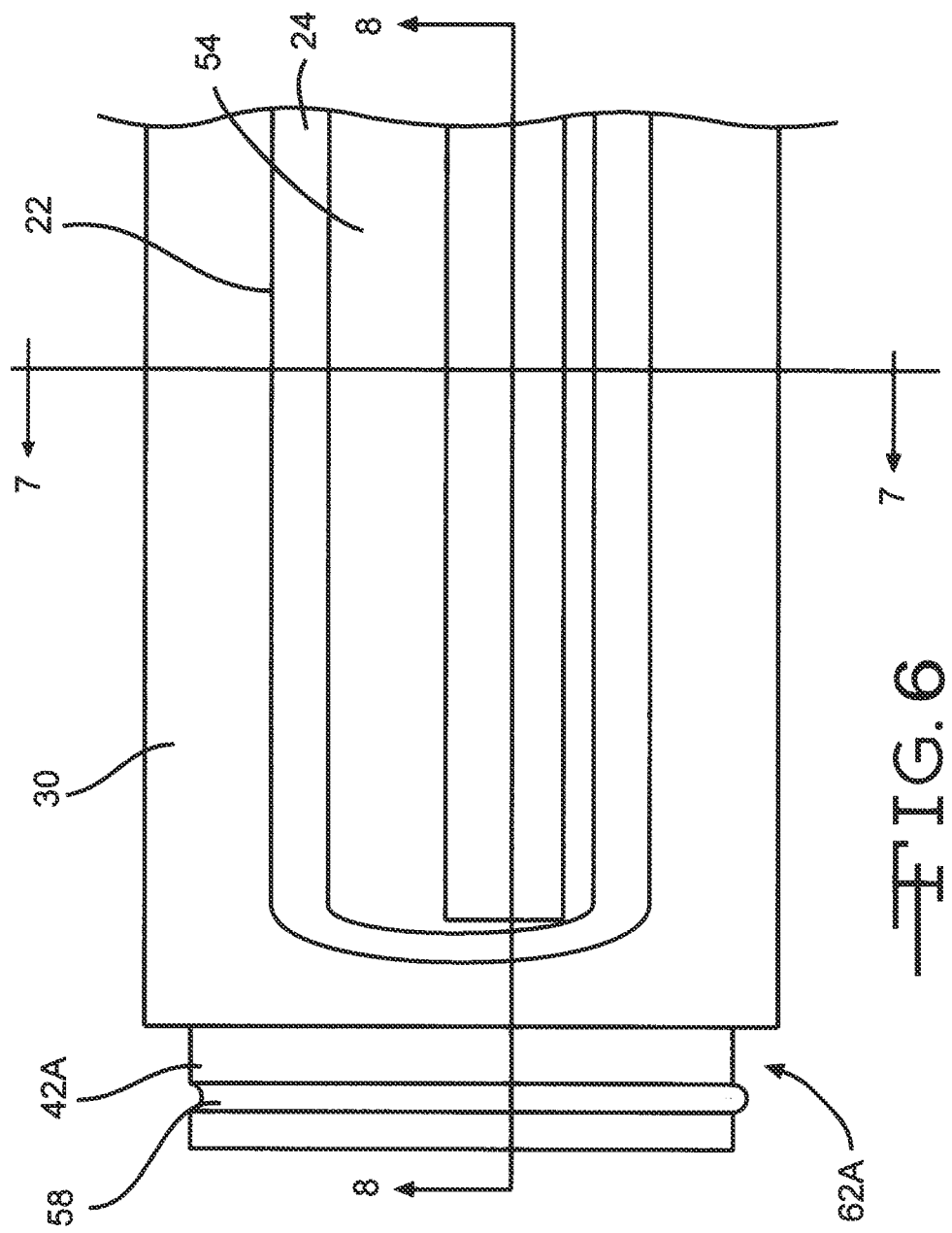

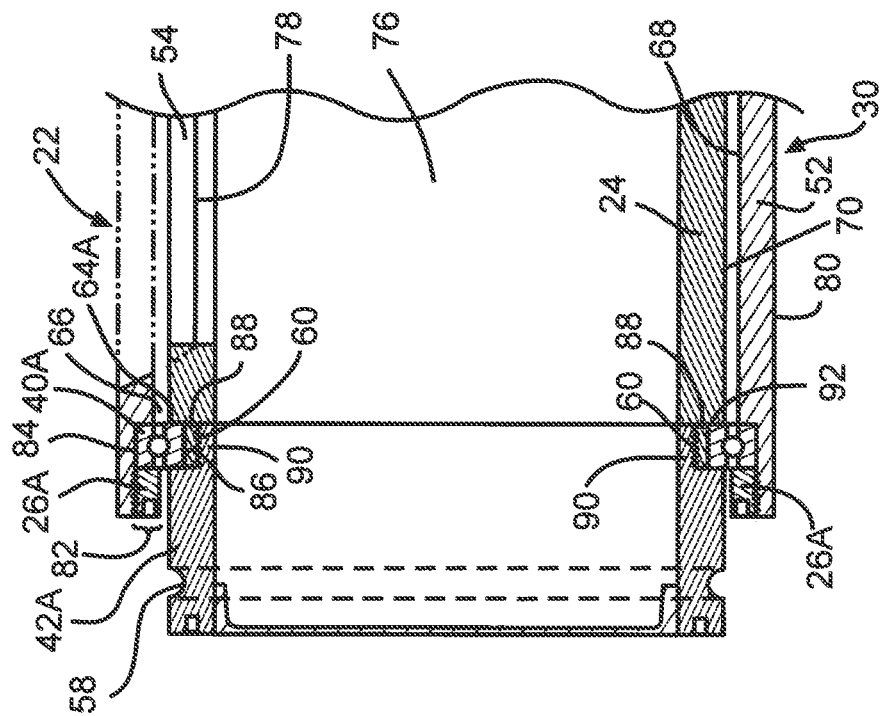
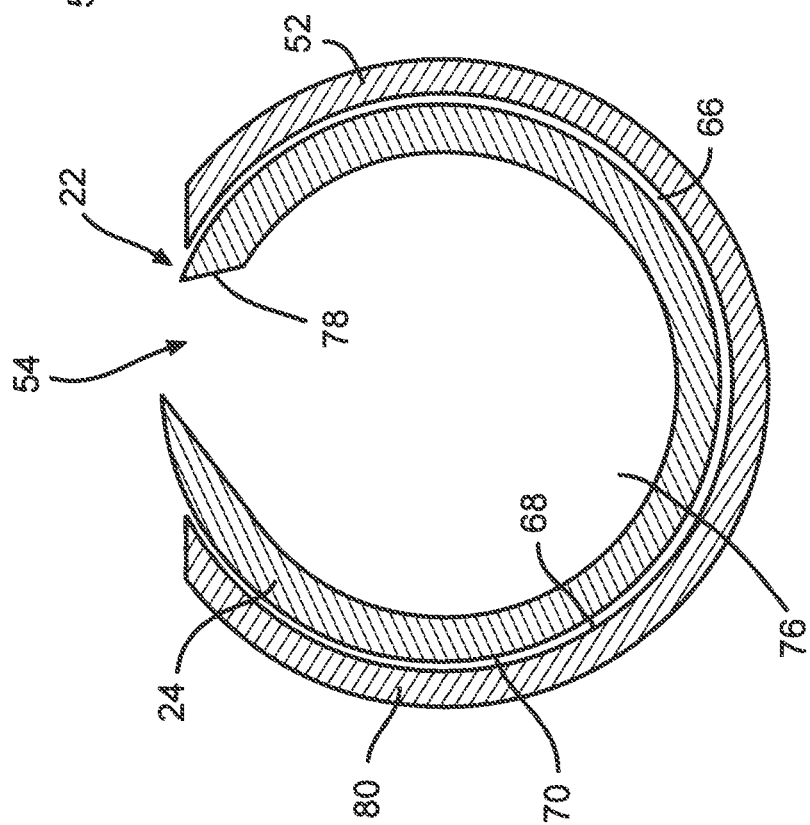

DISPOSABLE NEUCLEOTOMY SHAVER

CROSS-REFERENCE TO RELATED APPLICATIONS

This application claims priority from U.S. Provisional Patent Application Ser. No. 61/299,703, filed Jan. 29, 2009.

1. Field of the Invention

The present invention relates to the art of orthopedic tissue cutting devices, and more particularly, to a disposable shaver apparatus designed to remove spinal tissue.

2. Prior Art

In a surgical procedure commonly known as a "discectomy", nucleus pulposis tissue is removed from a disc that is situated between vertebral bodies of the spine. Depending on the surgery, a herniated portion of the nucleus pulposis outside the disc and/or variable size portions within the disc might be removed. A discectomy is typically performed during a spine fusion procedure. During this procedure a surgeon fenestrates the annulus of the targeted disc and removes extensive portions of its internal nucleus. This is done to prepare room for an interbody implant. An implant, such as a fusion cage with graft bone, bone growth substitute, or a combination thereof, is then inserted in the hollowed-out space.

Spinal fusion procedures continue to be popular because of their successful outcomes and ability to relieve back pain. Because they typically create less postoperative pain, and help expedite patient recovery time, minimally invasive spine fusion procedures are advancing in popularity at a very rapid pace. Despite this phenomenon, the emerging minimally invasive fusion procedures—particularly those that access the spine laterally—could benefit from the invention of some new, procedure-enhancing instrumentation. The present invention provides features that address this problem.

Because these spine fusion procedures require the insertion of an implant, a substantial amount of tissue in the intervertebral disc space must be removed or debulked. The debulking process requires that a large volume of tissue be removed to ensure that an implant can adequately fit in the intervertebral space. Traditionally, these fusion related disectomies have been performed using manual hand tools such as rongeurs, curettes, osteotomes and chisels. Hand held powered instruments such as drills and rotating burrs have been used as well. These hand tools are designed such that they only allow a small amount of tissue to be removed at a time. They are well-suited for removing small amounts of tissue in and around the spinal area, but are not well designed to quickly debulk a large amount of nucleus material in the disc space.

These tools typically have a small cutting surface with which to cut and remove tissue. Use of these tools requires a considerable amount of time to debulk the intervertebral space, as a small amount of tissue is removed at a time. For example, when using ronguers, each time that a surgeon inserts the tool into the disc space, it is only possible to "bite off" small portions of the nucleus. The tool is then retracted from the patient, extracting only small amounts of tissue. This procedure of cutting and extracting tissue is repeated until enough tissue has been debulked from the disc space to acceptably insert and fit the fusion cage. This time consuming activity exposes a patient to longer procedure times in the operating room. Prolonging the procedure is not desirable because it increases patient trauma and associated medical costs.

In addition, some hand tools may periodically require sharpening, and all of them need to be sterile for surgical use. This also applies to resharpened hand tools. Sterilization procedures may not always adequately prepare these hand tools for surgical use. There is always a possibility that the sterilization process may not thoroughly remove all possible infection agents such as bacteria. In addition, machining lubricants and other chemicals used during the re-sharpening process may not be sufficiently removed.

The present invention provides for a more efficient means of intervertebral body tissue removal. The present invention is designed to remove a large volume of tissue in a shorter period of time. As will be discussed in more detail, the shaver of the present invention is designed with a cylindrical cutting blade that provides for a larger, more efficient cutting surface. In addition, the tissue cutting blade of the present invention is oriented perpendicularly to its elongated body and drive mechanism. This design feature allows for greater access to the intervertebral tissue and therefore contributes to the present invention's increased tissue removal efficiency.

A further feature of the present invention is an ability to utilize blades with cutting teeth in different shapes and sizes. The ability to quickly swap-out blades with different cutting features provides the surgeon with an ability to adapt to a broader spectrum of tissue removal requirements.

The cutting features and physical shape of the invention can additionally be designed to facilitate a variety of spinal disectomy procedures. For example, although in a favored embodiment the invention is ideally suited to perform a discectomy in the lumbar region of the spine during a minimally invasive extreme/direct lateral interbody fusion procedure, it can be adapted to perform these functions effectively in other regions of the spine. It can also be adapted for other access approaches, including lateral, postolateral, and anterior. And, it can likewise be adapted for both traditional open and minimally invasive spine surgery.

Other powered shaver devices have been disclosed in U.S. Pat. No. 6,692,501 and U.S. patent application publication number 2010/0010525 to Michelson and Lockhard et al., respectively. These devices are designed with a series of "gear-like" cutters. Both devices described in the '501 patent and the 525 publication are limited in that their gear-like cutter blade design has a restricted tissue contact area. This restricted tissue contact impedes the tissue removal efficiency of these devices. In addition, unlike the present invention, these prior devices lack the ability to utilize tissue cutting blades of differing cutting surfaces, such as a serrated, a sharp edge surface, or combinations thereof.

An additional feature of the shaver of the present invention, unlike that of the prior art, is that tissue is removed along the width of the shaver blade. This feature allows for removal of tissue along a wider area, which results in an increased debulking rate as compared to the previously described instruments, both powered and non-powered. In addition, the perpendicular orientation of the blade to the elongated body and drive mechanism allows for increased tissue removal control in the intervertebral disc spaces. This preferred blade orientation, of the present invention, allows for easier access to the disc space tissue and further contributes to its removal efficiencies.

The ability to increase the intervertebral tissue removal rate is beneficial to the patient. An increased debulking rate reduces operating time, which translates into a reduction in patient trauma and associated medical costs. The gear-like blade design and parallel blade orientation of the prior art devices do not provide the increased tissue removal efficiencies of the present invention.

Furthermore, the tissue cutting device of the present invention can be made cost effectively, such that the device can be intended for a single use. The disposability feature of the present invention ensures that a sharp and sterile device is used for each procedure. The use of a dull and/or non-sterile device could potentially result in poor patient outcomes.

Thus, it is desired to provide a disposable spine shaver that removes disc tissue more efficiently than comparable devices described by the prior art. More efficient disc tissue removal reduces patient trauma and translates into reduced medical costs.

SUMMARY OF THE INVENTION

The present invention is a device designed to efficiently remove intervertebral disc tissue. More specifically, the present invention is designed to remove or debulk tissue in the intervertebral space, thus creating room for the insertion of an implant construct. The shaver device of the present invention comprises an elongated body with a proximal portion, a distal portion, and a longitudinal length therebetween. At the distal end of the device, residing within a blade enclosure, is a shaver blade. The shaver blade is preferably of a cylindrical shape designed to rotate freely inside the blade enclosure.

An opening extending longitudinally along the surface of the cylindrical shaver blade provides a tissue cutting surface. In a preferred embodiment, the wall thickness of the shaver blade opening is designed to provide the tissue cutting surface. However, the shape of the tissue cutting surface is not limited and may have a serrated, a razor thin, or a blunt surface. Such various tissue cutting surfaces may be utilized for different tissue removal requirements.

Annular bearings, preferably located at both ends of the blade enclosure, provide "guide rails" on which the cylindrical blade rotates. These annular bearings prevent the shaver blade from contacting the enclosure's inner wall surface or becoming askew in the enclosure. Such blade misalignments may obstruct blade rotation.

Both the cylindrical shaver blade and the blade enclosure have openings sized to allow tissue to enter. It is preferred that the two openings are aligned in such a way that they allow tissue to advance to the cutting surface of the shaver of the present invention.

A drive shaft extends perpendicularly through the proximal portion of the elongated body. Attached to the drive shaft is a drive gear. This gear is positioned such that its rotational movement is parallel to the elongated body. The rotational movement of the drive gear imparts rotational movement to the drive shaft.

Also attached to the drive shaft is a pulley. A drive belt is further connected to the pulley at the proximal portion and the shaver blade at the distal portion. The belt-and-pulley mechanism transmits torque from the drive shaft to the shaver blade. This transfer of torque results in rotation of the cylindrical shaver blade.

The present invention further comprises a central passageway located within the elongated body. The passageway extends from the proximal portion to the distal portion of the elongated body. This feature allows for the passage of tissue debris. In a preferred embodiment, a vacuum source is attached to the shaver's proximal end to provide efficient debris removal.

In a preferred embodiment, a power source such as an electric or pneumatic motor is attached to the proximal end of the device. The power source is designed to provide mechanical energy that rotates the drive gear.

The motor engages the drive gear which rotates the drive shaft. Rotational movement of the drive shaft rotates the drive belt which, in turn, rotates the cylindrical shaver blade located at the distal portion of the shaver.

The present invention is sized and dimensioned to easily be inserted into the body and provide direct access to the targeted tissue. The shaver of the present invention is designed such that the tissue cutting surface is located along the cylindrical blade's longitudinal axis. In addition, the shaver blade's longitudinal axis is oriented perpendicularly to its elongated body and drive mechanism. This preferred design feature of the present invention increases the rate of tissue removal.

Tissue is efficiently removed when in contact with the opening of the shave blade along the longitudinal axis. Therefore, the present invention makes it possible for a greater amount of intervertebral tissue to be removed within the path of the shaver blade. An increased rate of tissue removal increases debulking speed. An increased debulking speed is beneficial when performing certain spine procedures, particularly discectomies performed during minimally invasive lateral-access spine fusion procedures. During fusion related procedures such as this, a large volume of tissue between vertebrae is removed to allow space for the insertion of an intervertebral implant such as a fusion cage.

It is generally accepted that a larger sized implant provides increased spinal stability for the patient. Therefore, a larger implant requires more space, resulting in a need to debulk more tissue. The elongated cylindrical blade design of the present invention allows for an increased tissue removal rate, which therefore enables an implant to be inserted in a shorter amount of time. The shortened procedural time is less traumatic to the patient and reduces overall medical costs.

Accordingly, the present invention provides a cost effective spine shaver with a novel blade and drive belt mechanism that improves tissue removal efficiency. The enhanced reaming efficiencies of the present invention decrease procedural times and minimize patient trauma.

SUMMARY OF THE DRAWINGS

FIG. 2 is an exploded view illustrating the components comprising the internal assembly of the present invention.

FIG. 3 is a perspective view of the internal assembly of the present invention in a preferred assembled embodiment.

FIG. 3A is a perspective view illustration of an embodiment of the shaver blade insert, of the present invention.

FIG. 3B is a perspective view showing an alternatively preferred embodiment of the shaver blade of the present invention.

FIG. 6 is a magnified side view of a portion of the blade enclosure of the present invention.

FIG. 7 is a cross-sectional view taken along line 7-7 of the embodiment illustrated in FIG. 6.

FIG. 8 is a cross-sectional view taken along line 8-8 of the embodiment shown in FIG. 6.

DETAILED DESCRIPTION OF THE INVENTION

Figure 1:
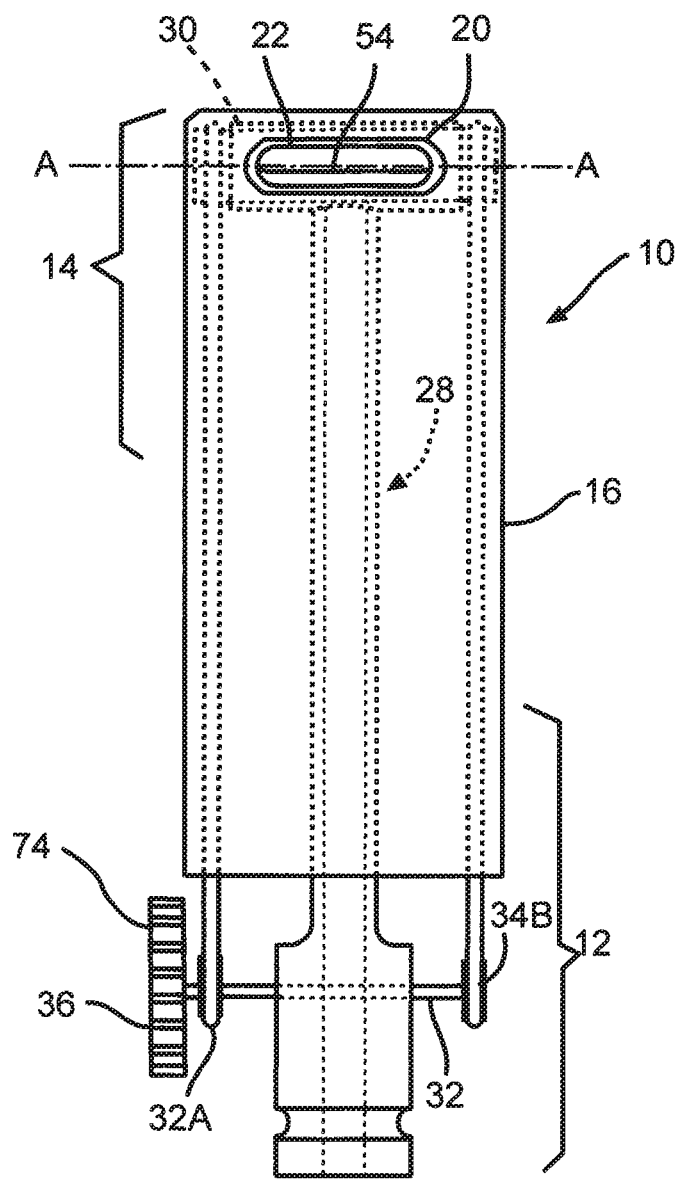
FIG. 1 is a side view, taken from the bottom side of the present invention.

Now turning to the figures, FIG. 1 illustrates a preferred embodiment of the spine shaver 10 of the present invention.

As illustrated in FIG. 1, the present spine shaver 10 has a length extending from a proximal portion 12 to a distal portion 14. The present invention further comprises an outer housing 16 that encloses an internal shaver assembly 18 (FIG. 3).

In a preferred embodiment, the outer housing 16 covers a portion of the internal assembly 18 from the device distal portion 14 to the device proximal portion 12. The outer housing 16 is preferably designed such that the portion of the device that is inserted into a human body is protected from undesired bodily contact. The outer housing 16 is designed to adequately isolate the internal assembly 18 from unintentional contact with body tissue and fluid while still providing a minimally invasive profile.

Alternatively, the outer housing 16 can be constructed such that the entire internal shaver assembly 18 is enclosed. The outer housing 16 illustrated in FIG. 1 is an exemplar of an outer housing 16 and is not to be construed as a limiting design of the present invention. It is also preferred that the outer housing 16 be constructed from a biocompatible material such as a biocompatible polymer or metal. Preferred biocompatible materials include, but are not limited to, poly (etheretherketone) (PEEK), acrylonitrile butadiene styrene (ABS), stainless steel, and titanium.

Figure 9:
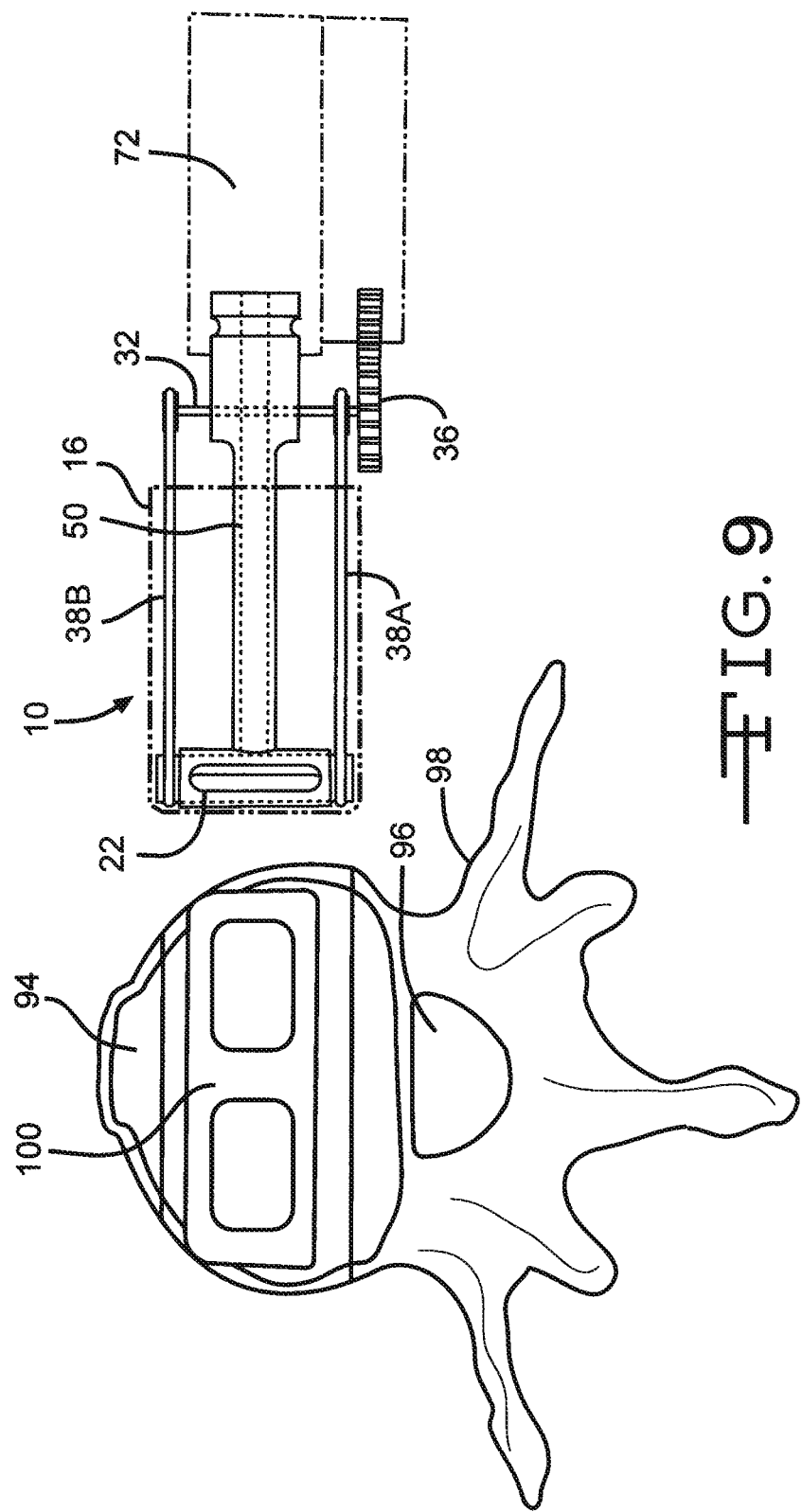
FIG. 9 is a cross-sectional view showing an implant positioned in an intervertebral space of the spine.

The outer housing 16 is sized to enclose the components of the internal shaver assembly 18 of the present invention while still allowing penetration to the targeted intervertebral tissue area 94 (FIG. 9). In a preferred embodiment, outer housing 16 has a length from about 10 cm to about 25 cm, a height from about 0.5 cm to about 10 cm and a width from about 1 cm to about 10 cm. It is also preferred that the outer housing have a wall thickness of about 0.5 mm to about 5 mm. This relatively thin outer wall housing thickness minimizes the overall size of the shaver device 10.

The shaver 10, as depicted in FIG. 1, has an outer housing blade opening 20. The outer housing opening 20 is positioned within the distal portion 14. The outer housing opening 20 extends widthwise across the distal portion 14 of the shaver device 10 along axis A-A. Opening 20 penetrates through the outer wall of the outer housing 16. The outer housing blade opening 20 is sized to allow tissue and/or bone to enter. It is preferred that the housing opening 20 aligns with a shaver blade enclosure opening 22 of an elongated body 28 of the internal assembly 18 (FIGS. 2, 3, 4 to 8, 8A and 9). The enclosure opening 22 is located beneath the outer housing 16. Alignment of the two openings 20, 22 is preferred to allow excised tissue to enter the shaver blade 24. In a preferred embodiment, housing opening 20 has a rectangular shape with a length from about 4 cm to about 10 cm and a width from about 4 cm to about 8 cm. The shape of the blade enclosure opening 22 is not limited and alternatively, can be round, oval, or triangular in shape.

FIG. 2 illustrates an exploded view of the components that comprise the internal assembly 18 of the shaver 10. As FIG. 2 shows, the internal assembly 18 comprises the elongated body 28, a shaver blade enclosure 30, a drive shaft 32, pulleys 34A, 34B, a drive gear 36, drive belts 38A, 38B, a shaver blade 24, annular bearings 40A, 40B, washers 26A, 26B and end caps 42A, 42B.

It should be noted that many of the components that comprise the shaver 10 have a left and a right side. Throughout this document, the left side feature is designated an "A" and the right side feature is designated a "B". For example, there is a left side drive belt 38A and a right side drive belt 38B. The accompanying figures may or may not illustrate both "A" and "B" side embodiments.

The elongated body 28 further comprises a body proximal portion 44, a body distal portion 46, and a body shaft or elongated length portion 48 therebetween. In a preferred embodiment, the body distal portion 46 is narrower than the body proximal portion 44. As shown in FIG. 2, the body proximal portion 44 fluidly transitions into the narrower shaft portion 46 as it further extends to the body distal portion 46.

It is preferred that the overall length of the elongated body 28 range from about 10 cm to about 50 cm. The length of the shaft portion 48 is dependent on the physical build of a person. A longer shaft portion 48 is preferred for an obese patient as opposed to a petite person. For example, for an obese person, the length of the shaft portion 48 may range from about 30 cm to about 50 cm whereas for a petite person, the length of the shaft portion 48 may range from about 10 cm to about 30 cm.

As illustrated in FIG. 2, it is preferred that body proximal portion 44 and shaft portion 48 have a rectangular shape. However, both the shaft 48 and proximal portions 44 may be constructed with a different shape such as round or oval.

In a preferred embodiment, a central passageway 50 extends from the body proximal portion 44, through the shaft portion 48 to the body distal portion 46. The central passageway 50 is designed such that debris can easily pass through from the body distal portion 46 through the shaft portion 48 and through the body proximal portion 44. The passageway opening 50 may be rectangular, round or circular such as it is shaped and sized to allow tissue debris to pass through. In a preferred embodiment, a vacuum source (not shown) can be attached to the end of the body proximal portion 44 or alternatively a vacuum tube (not shown) can be provided in the central passageway 50 to remove tissue and/or bone debris. In an alternately preferred embodiment, the vacuum tube (not shown) can be attached along the body shaft portion 48. Attaching the vacuum tube (not shown) along this portion of the present invention prevents possible obstruction of the vacuum tube (not shown) from the drive shaft 32.

The shaver blade enclosure 30 is provided within the body distal portion 46. Preferably the shaver blade enclosure 30 is an extension of the housing shaft 48 and is in fluid communication with the housing shaft 48. Enclosure 30 and body distal portion 46 are the same. Shaft passageway 50 extends into the shaver enclosure 30. As previously mentioned, a shaver blade opening 22 extends across the width of the blade enclosure 30 along axis B-B (FIG. 3). The opening 22 penetrates through the side wall 52 of the shaver blade enclosure 30. The opening 22 is sized to allow tissue and/or bone matter to enter. Preferably, the dimensions of the shaver blade opening 22 correspond with the dimensions of the cutting blade opening 54 of a shaver blade 24. However, the size and shape of the opening 22 of the shaver blade enclosure 30 do not necessarily have to be that of the cutting blade opening 54 but can encompass many shapes and sizes, not limited to round, elliptical, oblong or rectangular so as long as tissue can enter the blade opening 54.

It is contemplated that the present invention may have multiple blade openings 22 in the enclosure 30. Such an embodiment with multiple openings 22 provides additional tissue access. This alternative embodiment is beneficial when tissue is positioned at different orientations in the body. If multiple openings 22 are desired, the design would preferably include multiple housing openings 22 that correspond to housing openings 20. Multiple openings 20, 22 in both the blade enclosure 30 and shaver housing 16 provide additional tissue removal options and additional tissue removal efficiency.

It is preferred that both the elongated body 28 and the blade enclosure 30 are made from biocompatible materials such as a biocompatible polymer or metal. These biocompatible materials include, but are not limited to, poly(etheretherketone) (PEEK), acrylonitrile butadiene styrene (ABS), stainless steel, and titanium. These preferred biocompatible materials are desirable because they are lightweight, provide structural rigidity and are cost efficient.

The shaver blade 24 (FIGS. 2, 3A, 3B, 7, 8 and 8A) is designed and shaped to freely rotate within the enclosure 30. It is preferred that the shaver blade enclosure 30 be cylindrical, having dimensions that are slightly larger than the blade 24. These slightly larger dimensions of the enclosure 30 allow the blade 24 to freely rotate within the enclosure 30. The blade 24 is design to rotate in a unidirectional clockwise or counterclockwise direction or alternatively, oscillate between clockwise and counterclockwise directions. It is preferred that the enclosure 30 have a width from about 1 cm to about 10 cm and a diameter from about 0.5 cm to about 8 cm.

End caps 42A, 42B are preferably designed to attach to each end 56A, 56B of the shaver blade 24. End caps 42A, 42B provide a means to attach the drive belt 38A, 38B to the blade 24. It is preferred that the diameter of the end cap 42A, 42B is similar in size to that of the diameter of the shaver blade 24. In a preferred embodiment, end caps 42A, 42B have a diameter from about 0.5 cm to about 8 cm and a length from about 1 cm to about 5 cm. In addition, end caps 42A, 42B are designed such that when attached to the shaver blade 24, they extend past the ends 56A, 56B of the enclosure 30. The extended length of the end caps 42A, 42B provide a surface around which the drive belt 38 can be connected.

It is preferred that the shaver blade 24, end caps 42A, 42B and drive belts 38A, 38B be composed of a biocompatible material. It is further preferred that the shaver blade 24 and end caps 42A, 42B be constructed from a biocompatible material that includes, but is not limited to, poly(etheretherketone) (PEEK), acrylonitrile butadiene styrene (ABS), stainless steel, and titanium. It is also preferred that drive belts 38A, 38B and washers 26A, 26B be constructed from an elastic biocompatible material such as a silicone rubber.

At one end of each end cap 42A, 42B (FIGS. 2 and 6) is provided a groove 58A, 58B that circumferentially extends around the outer surface thereof. A drive belt 38A, 38B is preferably placed around the groove 58A, 58B as shown in FIG. 3. Opposite the groove 58A, 58B, each end cap 42A, 42B is provided with a threading 60 (FIGS. 2 and 6). This threading 60A, 60B is designed to mate with the corresponding threaded ends 56A, 56B of the shaver blade 24. Alternatively, the end caps 42A, 42B can be attached to the opposed ends 56A, 56B of the blade 24 by means of a mechanical interference fit, adhesive or over-molding connection.

It is preferred that two annular bearings 40A, 40B are positioned within the ends 62A, 62B of the insert blade enclosure 30. A washer 26A, 26B is placed over the respective end caps 42A, 42B adjacent to the annular bearings 40A, 40B. The washers 26A, 26B are designed to prevent the bearings 40A, 40B from moving laterally away from the blade 24. The annular bearings 40A, 40B provide guide rails 64A, 64B (FIG. 8) at the opposed blade ends 56A, 56B. The annular bearings 40A, 40B provide an offset space 66 between the interior wall surface 68 of the blade enclosure 30 and the outer surface 70 of the insert blade 24. These annular bearings 40A, 40B ensure that the insert blade 24 rotates freely within the enclosure 30 without coming into contact with the enclosure's interior wall surface 68. In addition, annular bearings 40A, 40B are designed to prevent the insert blade 24 from becoming askew or wobble in the enclosure 30.

FIG. 3 shows a preferred embodiment of the fully assembled internal shaver assembly 18 of the present invention. As the illustration shows, the shaver blade 24 is positioned in the blade enclosure 30. Drive belts 38A, 38B extend between the proximal and distal portions 44, 46. They are positioned around pulleys 34A, 34B in the proximal portion 44 and blade end cap grooves 58A, 58B in the distal portion 46. Drive gear 36 is positioned towards the proximal portion 12 of the shaver 10.

Preferably the drive gear 36 is attached to the drive shaft 32, positioned parallel to the proximal portion 44 of the body 28. The drive shaft 32 extends through the proximal portion 12 of the shaver 10, perpendicular to the shaft portion 48 of the elongated body 28. Rotation of the drive gear 36 rotates drive shaft pulleys 34A, 34B. This moves drive belts 38A, 38B which imparts rotational movement to the shaver blade 24. A motor 72 (FIG. 3) can be attached at the proximal end 44 to rotate drive gear 24. In a preferred embodiment, teeth 74 on the drive gear 34 engage with the motor 72. The motor 72 can be powered through various means, not limited to, electrical or pneumatic power. In a preferred embodiment, motor 72 is powered utilizing 120V or 110V corded electrical power. Alternately, the motor 72 can be powered utilizing self contained electrochemical batteries with various voltage, capacity, and current carrying capabilities. A self contained electrochemical powered motor 72 eliminates the need for a power cord which may obstruct the surgical procedure.

It is preferred that the drive mechanism, of the shaver 10 of the present invention, be designed with two parallel pulleys 34A, 34B and two drive belts 38A, 38B. However, it is contemplated that the present shaver 10 can be alternatively designed with a drive mechanism comprising a single pulley 34A or 34B and one corresponding drive belt 38A or 38B. The double pulley 34A, 34B and drive belt 38A, 38B design of the preferred embodiment provides additional robustness and durability to the shaver 10.

FIG. 3A illustrates a preferred embodiment of a shaver blade 24. As shown, the shaver blade 24 is of a cylindrical shape with a hollow cavity 76 (FIG. 7). A blade opening 54 preferably extends the width of the cylindrical blade 24 along axis C-C. The blade 24 preferably has a serrated tissue cutting surface 78. However, alternate cutting surfaces 78 such as a razor edge or blunt edge surface may also be designed.

Furthermore, cutting surface 78 may also be fabricated in a spiral pattern that circumferentially extends around the blade 24. This spiraled cutting surface 79 embodiment is shown in FIG. 3B. As the figure illustrates, the cutting surface 79 extends in a spiral orientation around the shaver blade 24 and extends the width of the blade 24. Similarly to the blade 24 embodiment shown in FIG. 3A, a blade opening 54 is provided between the cutting surface 79. Such a spiraled cutting surface 79 is beneficial in that it minimizes cutting resistance. In addition, these alternate cutting surfaces 78, 79 provide supplementary options that may be beneficial in removing various tissues and/or bone. The cutting surface 78 preferably extends along both sides of the blade opening 54. This preferred design enables tissue to be severed when the blade 24 is either rotated in clockwise, counter clockwise, or oscillative back and forth directions.

Figure 4:
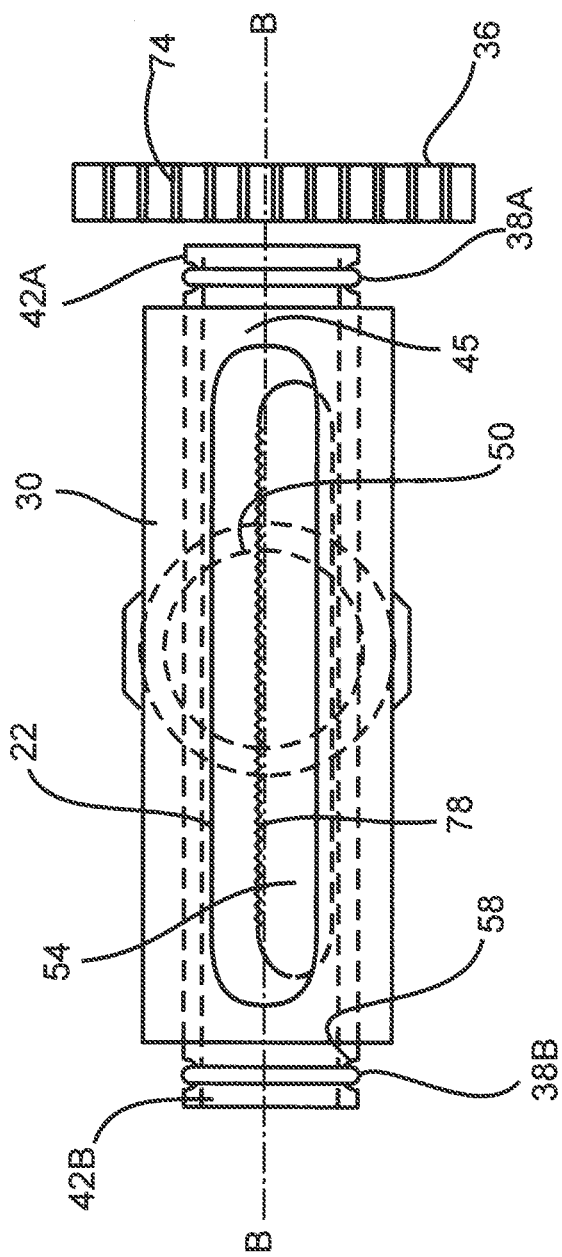
FIG. 4 is a side view, taken from the distal end, illustrating an alternately preferred embodiment of the blade enclosure.

FIG. 4 illustrates a preferred embodiment of the blade enclosure 30 of the internal assembly 18. As shown, the blade opening 22 in the enclosure portion 30 is positioned along the distal end 45 of the internal shaver assembly 18. The blade enclosure opening 22 is positioned at the distal end 45 of the internal assembly 18 to allow for tissue removal along a direct path into the intervertebral space 94. That way, the spine shaver 10 of the present invention is capable of removing disc tissue without rotating the device 10 itself.

Figure 5:
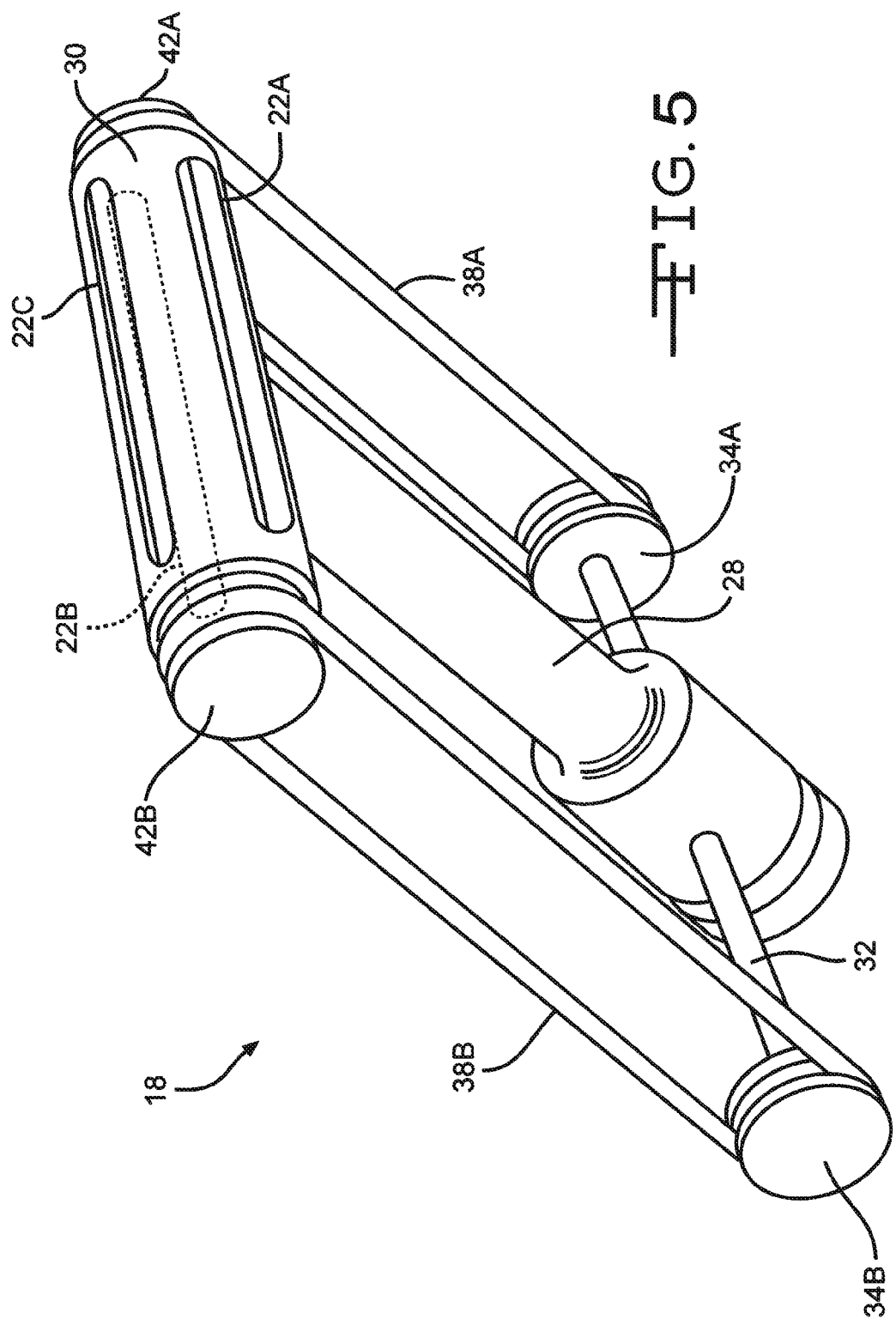
FIG. 5 is a perspective view illustrating an alternative embodiment of the present invention.

It is further contemplated that in an alternatively preferred embodiment, the shaver blade enclosure 30, has a plurality of three shaver blade openings 22A, 22B and 22C. This embodiment is illustrated in FIG. 5. As shown, the first shaver blade opening 22A is located along the bottom side of the enclosure 30. The second opening 22B is located along the top side of the enclosure 30, and the third opening 22C is along the distal end 45 of the enclosure 30. The combination of all three shaver blade openings 22A, 22B, and 22C allows for increased volumetric efficiency in excising tissue. This embodiment makes it possible to remove tissue in multiple directions at the same time. Therefore, the embodiment shown in FIG. 5 allows for an increased volume of tissue to be removed in the intervertebral space 94.

FIG. 6 illustrates a magnified view of a portion of an insert blade 24 residing in the blade enclosure 30. It is preferred that blade enclosure opening 22 has a length from about 4 cm to about 10 cm and a width from about 4 cm to about 8 cm. As shown, end cap 42A protrudes from an end 62A of the blade enclosure 30.

FIG. 7 shows a cross sectional view along line 7-7 of FIG. 6 of the shaver blade 24 residing in the blade enclosure 30. The insert blade 24 is preferably round and fits within the blade enclosure 30 without contacting the interior enclosure wall surface 68. As illustrated in FIG. 6, insert blade 24 has a blade opening 54 that is designed to allow tissue and bone to enter. The blade opening 54, as shown, has a razor thin cutting surface 78.

FIG. 8 illustrates a magnified cross-sectional view of the shaver blade 24 in the enclosure 30 along line 8-8 of FIG. 6. The shaver blade enclosure 30 has an interior wall surface 68 and an exterior wall surface 80. In a preferred embodiment of the present invention, the shaver blade 24 rotates within the enclosure 30 without contacting the interior wall surface 68. Such interference contact may result in undesirable wear of the insert blade 24 or make the shaver 10 inoperable.

Figure 8A:
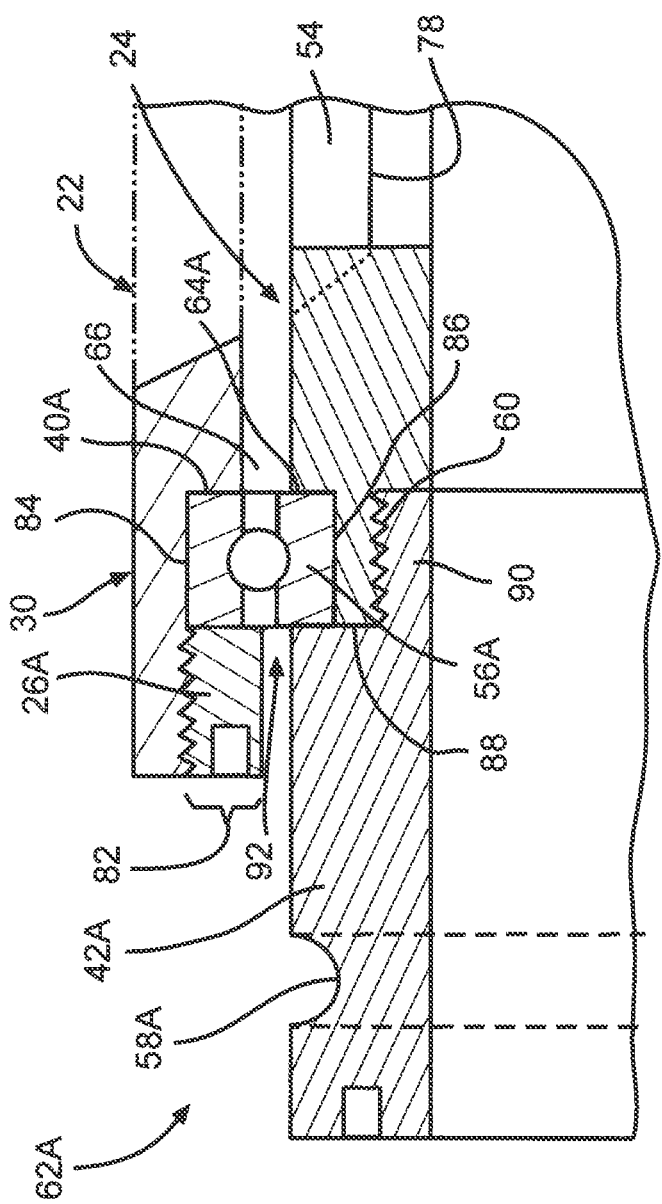
FIG. 8A is a magnified illustration showing the end portion of the shaver blade and blade enclosure embodiment.

FIG. 8A illustrates a magnified view of the top left portion of the blade 24 in enclosure 30. As illustrated, annular bearing 40A is positioned in a notch 82 at the end 62A of the enclosure 30. The notch 82 is a portion of the enclosure interior wall 68 that has been removed. The notch 82 circumferentially extends around each end 62A of the enclosure 30. Notch 82 may be preferably threaded as shown in FIG. 8A or alternatively have a smooth surface. A washer 26A is placed over the end cap 42A and advanced next to the annular bearing 40A in a snug fit. This washer 26A ensures that the annular bearing 40A does not move out of position. In a similar manner as the illustrated left portion of enclosure 30, a circumferential notch 82 resides on the right side for receiving bearing 40B.

An annular bearing 40A, 40B resides in each notch 82 of the enclosure 30. As shown in FIGS. 8 and 8A, surface 86 of the outer diameter of the annular bearing 40A seats in the notch 82 of the enclosure 30. In a preferred embodiment, a portion of the notch 82 is threaded to threadingly receive cap 26A. These threads are laterally outwardly from an unthreaded portion of the notch 82 which receives the bearing 40A. Alternatively, the outer diameter 82 of the annular bearing 40A, 40B and notch 82 can have an interference fit.

The inner diameter surface 86 of the annular bearing 40A, 40B resides in a recess portion 88 of the blade 24. The recess portion 88 is an area in which material has been removed from the ends 56A, 56B of the insert blade 24. The recess portion 88 circumferentially extends around the ends 56A, 56B of the shaver blade 24. The inner diameter surface 86 of the annular bearing 40A that protrudes from the inner wall 68 of the enclosure 30 provides a "guide rail" on which the ends 56A and 56B of the shaver blade 24 reside.

As shown in FIG. 8A, the end cap 42A has been threaded onto the end 56A of the shaver blade 24. A lip 90 feature provided on the end cap 42A prevents lateral movement of the shaver blade 24 in the enclosure 30. When correctly positioned, the end cap lip 90 and recessed portion 88 of the shaver blade 24 provide a groove 92 in which the inner diameter 86 of the annular bearing 40A resides. This design feature of the annular bearing 40A in combination with the end cap lip 90 and recessed portion 88 of the shaver blade 24 keeps the shaver blade 24 in place and enables it to rotate freely without contacting the enclosure interior wall surface 68 or becoming askew.

In operation, the shaver 10 of the present invention is preferably used in a discectomy procedure where it is desirable to remove tissue from the disc space between vertebrae. Such is the case during a minimally invasive lateral lumbar interbody fusion procedure.

In a minimally invasive lateral lumbar interbody fusion procedure, the shaver 10 would typically be inserted into the body from an "extreme" or "direct" lateral position. As shown in FIG. 9, by inserting the shaver 10 from the lateral side, the surgeon is able to achieve access to the targeted lumbar disc space 94 while avoiding damage to the spinal cord 96 and peripheral nerve tissue 98. Using a lateral approach, the surgeon is able to navigate through fibers of the psoas muscle, not cutting through it, and carefully advance past nerve obstacles with the help of neuromonitoring equipment. Because the lateral access approach successfully minimizes trauma and postoperative pain, it continues to enjoy increasing acceptance in the clinical community.

FIG. 9 illustrates a situation where the reamer 10 has been removed from a body and an implant 100 inserted into the cavity 94 created by the shaver 10. When the shaver path and width of the implant 100 are of a similar length, an optimized efficient removal of vertebral tissue is achieved. As such, a minimum number of shaver passes is required to create space for implant 100 insertion.

During the implant procedure, an access corridor is first established. This access corridor preferably extends from the side of a patient to the targeted spine area. The access corridor is dimensioned such that the shaver 10 of the present invention can advance to the targeted disc space of the patient. Once the targeted area has been reached, the shaver blade 24 and vacuum source are activated. Once the shaver blade 24 begins rotating, the shaver 10 is advanced between the vertebrae. After a sufficient amount of tissue has been removed, the shaver 10 is extracted from the patient. The implant 100 is then inserted into the debulked space.

Alternatively, the shaver 10 can be advanced from the anterior of the patient to the spine. In this alternate method, the access corridor for a lumbar spine fusion procedure could be through the patient's abdominal area.

Thus, it has been shown that the shaver 10 of the present invention provides faster, more efficient tissue removal from the intervertebral disc space 94. The features of the present invention, such as the cylindrical shaver blade 24 and perpendicular blade orientation, provide improved tissue removal efficiencies. In addition, the wider shaver blade cutting surface 78 provides a wider tissue cutting path that results in a faster debulking process, particularly during minimally invasive laterally accessed interbody fusion surgeries.

What is claimed is:

1. A device for cutting spinal tissue, the device comprising:
   a) an elongated body having a central passageway extending along a longitudinal axis from a distal body portion to a proximal body portion having a proximal open end;
   b) a drive shaft supported at the proximal body portion, perpendicular to the longitudinal axis of the body;
   c) a blade enclosure supported at the distal body portion and comprising an enclosure sidewall extending along an enclosure axis, wherein the blade enclosure comprises a first enclosure opening and a second enclosure opening in open communication with the central passageway of the body, and wherein at least a portion of a first perimeter of the first enclosure opening provides an enclosure cutting surface;
   d) a shaver blade comprising a cylindrically-shaped blade sidewall extending along a blade axis, wherein a blade opening in the blade sidewall is defined by a second perimeter with at least a portion of the second perimeter providing a tissue cutting surface, and wherein the shaver blade is rotatably positioned within the blade enclosure;
   e) a drive belt connecting the shaver blade to the drive shaft; and
   f) wherein a rotational force imparted to the drive shaft causes the drive belt to effect rotational movement the shaver blade to thereby cause the tissue cutting surface to rotatably move into a closely-spaced cutting relationship with the enclosure cutting surface to thereby cut tissue that is then movable along the central passageway of the body to the proximal open end thereof.

2. The device of claim 1 wherein the tissue cutting surface is selected from the group consisting of a serrated surface, a razor thin surface, a blunt surface and combinations thereof.

3. The device of claim 1 wherein the tissue cutting surface extends axially along a portion of the width of the shaver blade.

4. The device of claim 1 wherein the tissue cutting surface has a spiral orientation that extends circumferentially at least part way around the shaver blade.

5. The device of claim 1 wherein an annular bearing resides between an interior surface of the shaver blade enclosure and a recessed portion of the shaver blade.

6. The device of claim 1 wherein an end cap is attached to an end of the shaver blade.

7. The device of claim 6 wherein the drive belt is placed in a groove that circumferentially extends around the end cap.

8. The device of claim 1 wherein an outer housing covers the elongated body, the outer housing extending from the shaver distal portion to the body proximal portion.

9. The device of claim 8 wherein an outer housing opening extends through a sidewall of the outer housing such that both the blade enclosure opening and the outer housing opening align allowing tissue to enter.

10. The device of claim 1 wherein a motor, connectable to the proximal portion of the elongated body, engages the drive shaft.

11. The device of claim 1 wherein a vacuum source is connectable to the proximal portion of the elongated body.

12. The device of claim 1 wherein the elongated body and shaver blade are composed of a biocompatible material.

13. The device of claim 1 wherein the longitudinal axis of the body intersects the blade axis at a perpendicular orientation.

14. The device of claim 1 wherein the longitudinal axis of the body is perpendicular to the enclosure axis and the blade axis.

15. The device of claim 1 wherein the enclosure axis and the blade axis are co-linear.

16. A method of removing tissue between vertebrae, the method comprising:
   a) providing a shaver device, the device comprising:
      i) an elongated body having a central passageway extending along a longitudinal axis from a distal body portion to a proximal body portion having a proximal open end;
      ii) a drive shaft supported at the proximal body portion, perpendicular to the longitudinal axis of the body;
      iii) a blade enclosure supported at the distal body portion and comprising an enclosure sidewall extending alone an enclosure axis, wherein the blade enclosure comprises a first enclosure opening and a second enclosure opening in open communication with the central passageway of the body, and wherein at least a portion of a first perimeter of a first perimeter of the first enclosure opening provides an enclosure cutting surface;
      iv) a shaver blade comprising a cylindrically-shaped blade sidewall extending along a blade axis, wherein a blade opening in the blade sidewall is defined by a second perimeter with at least a portion of the second perimeter providing a cutting tissue surface, and wherein the shaver blade is rotatably positioned within the blade enclosure;
      v) a drive belt connecting the shaver blade to the drive shaft; and
      vi) wherein a rotational force imparted to the drive shaft causes the drive belt to effect rotational movement of the shaver blade to rotatably move into a closely-spaced cutting relationship with the enclosure cutting surface to thereby cut tissue that is then movable along the central passageway of the body to the proximal open end thereof;
   b) creating an access corridor extending from outside a patient to the spinal area;
   c) advancing the shaver device through the access corridor;
   d) removing tissue with the shaver device; and
   e) retracting the shaver device from the access corridor.

17. The method of claim 16 further attaching a motor, to the proximal portion of the elongated body that engages the drive shaft.

18. The method of claim 16 further attaching a vacuum source to the proximal portion of the elongated body.

19. The method of claim 16 further inserting an implant in a cavity created by the shaver device.

20. A method of manufacturing a device for cutting spinal tissue, the method comprising:
   a) providing an elongated body having a central passageway extending along a longitudinal axis from a distal body portion to a proximal body portion having a proximal open end;
   b) inserting a drive shaft supported at the proximal body portion, perpendicular to the longitudinal axis of the body;
   c) providing a shaver blade comprising a cylindrically-shaped blade sidewall extending along a blade axis, wherein a blade opening in the blade sidewall is defined by a second perimeter with at least a portion of the second perimeter providing a cutting tissue surface, and wherein the shaver blade is rotatably positioned within the blade enclosure; and
   d) connecting a drive belt to the shaver blade and drive shaft, wherein when a rotational force is imparted to the drive shaft, rotational movement of the drive shaft causes the drive belt to effect rotational movement of the shaver blade to rotatably move into a closely spaced cutting relationship with the enclosure cutting surface to thereby cut tissue that is then movable along the central passageway of the body to the proximal open end thereof.

21. The method of claim 20 further providing the tissue cutting surface selected from the group consisting of a serrated surface, a razor thin surface, a blunt surface and combinations thereof.

22. The method of claim 20 further providing an outer housing covering the elongated body, the outer housing extends from the shaver blade enclosure to a portion of the body proximal portion.

23. The method of claim 22 further creating an outer housing opening that extends through a sidewall of the outer housing such that both the blade enclosure opening and the outer housing opening align allowing tissue to enter.

24. A device for cutting spinal tissue, the device comprising:
   a) an elongated body having a central passageway extending along a longitudinal axis from a distal body portion to a proximal body portion having a proximal open end;
   b) a drive shaft supported at the proximal body portion, having a right drive shaft end extending to an opposite left drive shaft end, positioned perpendicular to the longitudinal axis of the body, a shaft pulley attached to either one of the left or right drive shaft ends;
   c) a blade enclosure supported at the distal body portion and comprising an enclosure sidewall extending along an enclosure axis, wherein the blade enclosure comprises a first enclosure opening and a second enclosure opening in open communication with the central passageway of the body, and wherein the first enclosure opening extends lengthwise along the enclosure axis and penetrates through the enclosure sidewall;
   d) a shaver blade comprising a cylindrically-shaped blade sidewall extending along a blade axis, the blade axis positioned about perpendicular to the longitudinal axis, wherein a blade opening in the blade sidewall is defined by a second perimeter with at least a portion of the second perimeter providing a tissue cutting surface, and wherein the shaver blade is rotatable about the blade axis within the blade enclosure, an end cap attached to either a right or left shaver blade end;
   e) a drive belt connecting the shaver blade to the drive shaft, the drive belt positioned around the end cap located at the distal end and around the shaft pulley at the proximal end;
   f) a drive gear attached to either the right or left drive shaft ends; and
   g) wherein a rotational movement of the drive gear causes the drive shaft and drive belt to effect rotational movement of the shaver blade to thereby cause the tissue cutting surface to rotatably move to thereby cut tissue that is then movable along the central passageway of the body to the proximal open end thereof.

25. The device of claim 24 wherein the tissue cutting surface is selected from the group consisting of a serrated surface, a razor thin surface, a blunt surface and combinations thereof.

26. The device of claim 24 wherein the tissue cutting surface extends axially along a portion of the width of the shaver blade.

27. The device of claim 24 wherein the tissue cutting surface has a spiral orientation that extends circumferentially at least part way around the shaver blade.

28. A device for cutting spinal tissue, the device comprising:
   a) an elongated body having a central passageway extending along a longitudinal axis from a distal body portion to a proximal body portion having a proximal open end;
   b) a drive shaft supported at the proximal body portion, perpendicular to the longitudinal axis of the body;
   c) a blade enclosure supported at the distal body portion and comprising an enclosure sidewall having a first enclosure opening having a first opening axis aligned perpendicular to the longitudinal axis of the body and a second enclosure opening in open communication with the central passageway of the body, wherein at least a portion of a first perimeter of the first enclosure opening provides an enclosure cutting surface;
   d) a shaver blade comprising a cylindrically-shaped blade sidewall extending along a blade axis, wherein a blade opening is defined by a second perimeter of the blade sidewall with at least a portion of the second perimeter providing a tissue cutting surface;
   e) wherein the shaver blade is rotatably positioned within the blade enclosure with the enclosure axis and the blade axis being co-linear, and
   f) wherein a rotational force imparted to the drive shaft causes a drive belt to effect rotational movement of the shaver blade to thereby cause the tissue cutting surface to rotatably move into a closely-spaced cutting relationship with the enclosure cutting surface to thereby cut tissue that is then movable along the central passageway of the body to the proximal open end thereof.

29. A device for cutting spinal tissue, the device comprising: an elongated body having a central passageway extending along a longitudinal axis from a distal body portion to a proximal body portion having a proximal open end;
   a drive shaft supported at the proximal body portion, perpendicular to the longitudinal axis of the body;
   a blade enclosure supported at the distal body portion and comprising an enclosure sidewall extending along an enclosure axis and comprising a first enclosure opening and a second enclosure opening in open communication with the central passageway of the body;
   a shaver blade comprising a cylindrically-shaped blade sidewall extending along a blade axis, wherein a blade opening in the blade sidewall is defined by a second perimeter with at least a portion of the second perimeter providing a tissue cutting surface;
   wherein the shaver blade is rotatably positioned within the blade enclosure with the enclosure axis and the blade axis being co-linear, and wherein a rotational force imparted to the drive shaft cause a drive belt to effect rotational movement of the shaver blade causing the tissue cutting surface to rotatably move to thereby cut tissue that is then movable along the central passageway of the body to the proximal end thereof.

\* \* \* \* \*

UNITED STATES PATENT AND TRADEMARK OFFICE
CERTIFICATE OF CORRECTION

| | |
|---|---|
| PATENT NO. | : 8,465,490 B1 |
| APPLICATION NO. | : 13/015714 |
| DATED | : June 18, 2013 |
| INVENTOR(S) | : Patrick M. White, Robert Siegler and James Hetherwick |

It is certified that error appears in the above-identified patent and that said Letters Patent is hereby corrected as shown below:

In the Specification

Column 1, line 7, delete "2009" and insert --2010--

In the Claims

Column 11, line 26 (Claim 1, line 25) after the word "movement" insert --of--

Column 12, line 14 (Claim 16, line 12) delete "alone" and insert --along--

Column 12, line 18 (Claim 16, line 16) before the words "of the" delete the words "of a first perimeter"

Column 14, line 38 (Claim 29, line 2) after the word "comprising:" delete the words "an elongated body having a central passageway extending along a longitudinal axis from a distal body portion to a proximal body portion having a proximal open end;"

Column 14, line 39 (Claim 29, line 3) insert --a) an elongated body having a central passageway extending along a longitudinal axis from a distal body portion to a proximal body portion having a proximal open end;--

Column 14, line 41 (Claim 29, line 5) before the words "a drive shaft" insert --b)--

Column 14, line 43 (Claim 29, line 7) before the words "a blade enclosure" insert --c)--

Column 14, line 47 (Claim 29, line 11) delete "body;" and insert --body, wherein at least a portion of a perimeter of the first enclosure opening provides an enclosure cutting surface--

Signed and Sealed this
Third Day of June, 2014

Michelle K. Lee
*Deputy Director of the United States Patent and Trademark Office*

CERTIFICATE OF CORRECTION (continued)
U.S. Pat. No. 8,465,490 B1

Column 14, line 39 (Claim 29, line 12) before the words "a shaver blade" insert --d)--

Column 14, line 39 (Claim 29, line 17) before the words "wherein the shaver" insert --e)--